United States Patent
Tanaka

[11] Patent Number: 5,885,737
[45] Date of Patent: Mar. 23, 1999

[54] HYDROXYGALLIUM PHTHALOCYANINE COMPOUND, PRODUCTION PROCESS THEREFOR AND ELECTROPHOTOGRAPHIC PHOTOSENSITIVE MEMBER USING THE COMPOUND

[75] Inventor: Masato Tanaka, Shizuoka-ken, Japan

[73] Assignee: Canon Kabushiki Kaisha, Tokyo, Japan

[21] Appl. No.: 837,212

[22] Filed: Apr. 22, 1997

[30] Foreign Application Priority Data

Apr. 26, 1996 [JP] Japan ................................ 8-129288

[51] Int. Cl.$^6$ ................................... G03G 5/047
[52] U.S. Cl. ................... 430/59; 430/56; 430/58; 430/78; 399/111; 399/116; 399/159; 540/140; 540/141
[58] Field of Search ................. 430/78, 56, 58, 430/59; 399/111, 116, 159; 540/140, 141

[56] References Cited

U.S. PATENT DOCUMENTS

| | | | |
|---|---|---|---|
| 5,302,479 | 4/1994 | Daimon et al. | 430/78 |
| 5,384,625 | 1/1995 | Amayama et al. | 355/211 |
| 5,407,766 | 4/1995 | Mayo et al. | 430/58 |
| 5,459,004 | 10/1995 | Katsumi et al. | 430/78 |
| 5,463,043 | 10/1995 | Nukuda et al. | 540/141 |
| 5,482,811 | 1/1996 | Keoshkerian et al. | 430/58 |
| 5,567,558 | 10/1996 | Hsiao et al. | 430/58 |

FOREIGN PATENT DOCUMENTS

| | | |
|---|---|---|
| 0617091 | 9/1994 | European Pat. Off. . |
| 0655655 | 5/1995 | European Pat. Off. . |
| 50-38543 | 10/1975 | Japan . |
| 51-108847 | 9/1976 | Japan . |
| 53-37423 | 4/1978 | Japan . |
| 5-263007 | 10/1993 | Japan . |
| 6-93203 | 4/1994 | Japan . |

*Primary Examiner*—Janis L. Dote
*Attorney, Agent, or Firm*—Fitzpatrick, Cella, Harper & Scinto

[57] ABSTRACT

An electrophotographic photosensitive member having a high sensitivity to long-wavelength light as emitted by a semiconductor laser and causing little change in potential change during repetitive use is formed by using as a charge-generating material a hydroxygallium phthalocyanine having a crystal form characterized by a strongest peak at a Bragg angle (2θ±0.2 deg.) of 28.1 deg. in a CuK$_\alpha$ characteristic X-ray diffraction pattern. The hydroxygallium phthalocyanine may preferably be produced through a process including treating a halogenated gallium phthalocyanine for conversion into a hydrous hydroxygallium phthalocyanine, freeze-drying the hydrous hydroxygallium phthalocyanine into a low-crystallinity hydroxygallium phthalocyanine, and milling the low-crystallinity hydroxygallium phthalocyanine.

7 Claims, 6 Drawing Sheets

HYDROXYGALLIUM PHTHALOCYANINE COMPOUND, PRODUCTION PROCESS THEREFOR AND ELECTROPHOTOGRAPHIC PHOTOSENSITIVE MEMBER USING THE COMPOUND

FIELD OF THE INVENTION AND RELATED ART

The present invention relates to a novel hydroxygallium phthalocyanine compound, a process for production thereof, an electrophotographic photosensitive member using the hydroxygallium phthalocyanine compound, and an electrophotographic apparatus and a process cartridge including the photosensitive member.

Hitherto, phthalocyanine pigments have been noted and studied not only as coloring agents but also as electronic materials for constituting electrophotographic photosensitive members, solar batteries, photosensors, etc.

On the other hand, printers utilizing electrophotography have been widely used as terminal printers in recent years. These printers are principally constituted as laser beam printers using a laser as a light source. As the light source, a semiconductor laser has been predominantly used in view of its cost and apparatus size. A semiconductor laser principally used at present has an emission wavelength in a long wavelength region of 790–820 nm, so that electrophotographic photoconductors having a sufficient sensitivity to such a long-wavelength light have been developed.

The sensitivity of an electrophotographic photoconductor varies depending on a charge-generating material, and many studies have been made on charge-generating materials having a sensitivity to a long-wavelength light including metallic phthalocyanines and non-metallic phthalocyanines, such as aluminum chlorophthalocyanine, chloroindium phthalocyanine, oxyvanadium phthalocyanine, hydroxygallium phthalocyanine, chlorogallium phthalocyanine, magnesium phthalocyanine, and oxytitanium phthalocyanine.

Many of these phthalocyanine compounds are known to have various crystal forms. For example, non-metallic phthalocyanine is known to have α-form, β-form, γ-form, δ-form, ε-form, χ-form, τ-form, etc., and copper phthalocyanine is known to have α-form, β-form, γ-form, δ-form, χ-form, etc. Specific examples of these phthalocyanine compounds are disclosed in, e.g., Japanese Laid-Open Patent Application (JP-A) 50-38543, JP-A 51-108847, and JP-A 53-37423.

As for hydroxygallium phthalocyanine, several crystal forms have been disclosed in, e.g., JP-A 5-263007 and JP-A 6-93203. However, electrophotographic photosensitive members prepared by using such hydroxygallium phthalocyanine compounds have not been used in high-speed and high-image quality electrophotographic processes, because of unsatisfactory sensitivity, potential stability in repetitive use, and memory characteristic in response to white light.

SUMMARY OF THE INVENTION

A principal object of the present invention is to provide a novel crystal form of hydroxygallium phthalocyanine (compound).

Another object of the present invention is to provide an electrophotographic photosensitive member using such a hydroxygallium phthalocyanine and showing a high sensitivity to long-wavelength rays and little potential change during repetitive use.

Another object of the present invention is to provide an electrophotographic photosensitive member free from photomemory even when illuminated with visible rays for a long period.

A further object of the present invention is to provide a process cartridge and an electrophotographic apparatus including such an electrophotographic photosensitive member.

According to the present invention, there is provided a hydroxygallium phthalocyanine having a crystal form characterized by a strongest peak at a Bragg angle (2θ±0.2 deg.) of 28.1 deg. in a $CuK_\alpha$ characteristic X-ray diffraction pattern.

According to another aspect of the present invention, there is provided a process for producing a hydroxygallium phthalocyanine, comprising the steps of:

treating a halogenated gallium phthalocyanine for conversion into a hydrous hydroxygallium phthalocyanine, freeze-drying the hydrous hydroxygallium phthalocyanine into a low-crystallinity hydroxygallium phthalocyanine, and milling the low-crystallinity hydroxygallium phthalocyanine.

According to the present invention, there is further provided an electrophotographic photosensitive member, comprising: an electroconductive support, and at least a photosensitive layer formed on the electroconductive support containing the above-mentioned hydroxygallium phthalocyanine.

According to the present invention, there is also provided an electrophotographic apparatus, comprising: the above-mentioned electrophotographic photosensitive member, charging means for charging the photosensitive member, imagewise exposure means for exposing imagewise the photosensitive member to form an electrostatic latent image into the photosensitive member, and developing means for developing the electrostatic latent image on the photosensitive member with a toner.

The present invention further provides a process cartridge, comprising: the above-mentioned electrophotoqraphic photosensitive member and a charging means for charging the photosensitive member so as to form an integral unit, which is detachably mountable to a main assembly of an electrophotographic apparatus.

These and other objects, features and advantages of the present invention will become more apparent upon a consideration of the following description of the preferred embodiments of the present invention taken in conjunction with the accompanying drawings, wherein like parts are denoted by like reference numerals.

DETAILED DESCRIPTION OF THE INVENTION

Figure 1:
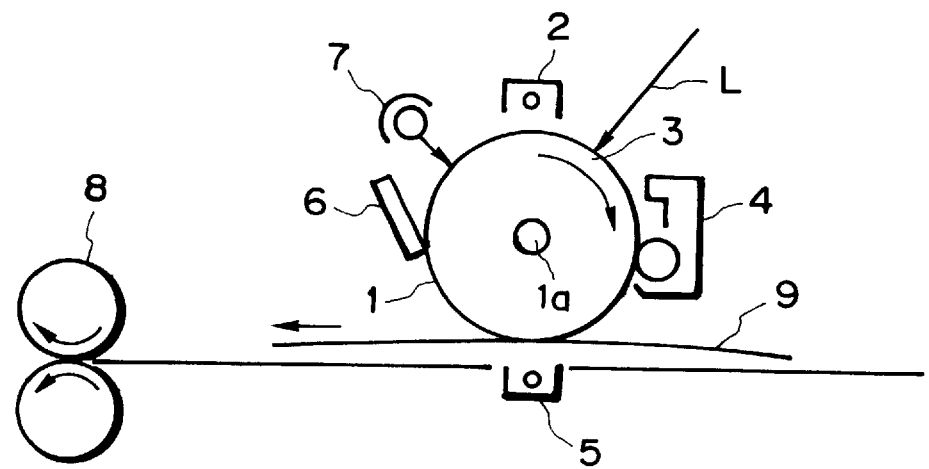
FIGS. 1–4 are respectively a schematic illustration of an embodiment of the electrophotographic apparatus according to the invention.

The hydroxygallium phthalocyanine according to the present invention has a chemical structure as represented by the following formula and is characterized by a strongest peak (i.e., a highest peak) at a Bragg angle (2θ±0.2 deg.) of 28.1 deg. in a CuK$_\alpha$ characteristic X-ray diffraction pattern:

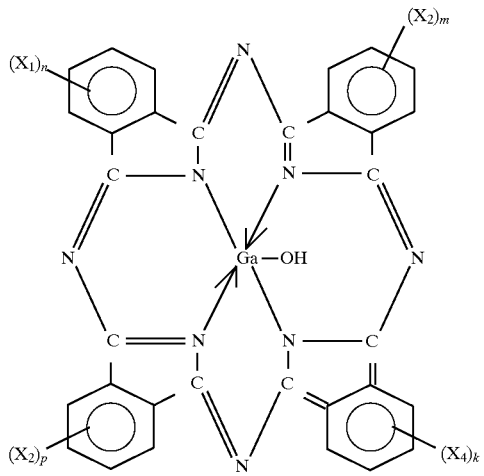

wherein $X_1$, $X_2$, $X_3$ and $X_4$ respectively denote Cl or Br, and n, m, p and k respectively denote an integer of 0–4.

The hydroxygallium phthalocyanine according to the present invention may also have peaks at Bragg angles of 7.3 deg., 24.9 deg., etc., in addition to the peak at 28.1 deg., but these peaks are all lower than the one at 28.1 deg.

By using the hydroxygallium phthalocyanine as a charge-generating material in an electrophotographic photosensitive member, it is possible to obtain an electrophotographic photosensitive member having a high sensitivity to long-wavelength light, excellent durability and also an improved memory characteristic.

The X-ray diffraction data referred to herein for determining the crystal form of hydroxygallium phthalocyanine according to the present invention are based on data measured by X-ray diffractometry using CuK$_\alpha$ characteristic X-rays according to the following conditions:

Apparatus: Full-automatic X-ray diffraction apparatus ("MXP18", available from MAC Science K.K.)

X-ray tube (Target): Cu
Tube voltage: 50 kV
Tube current: 300 mA
Scanning method: 2θ/θ scan
Scanning speed: 2 deg./min.
Sampling interval: 0.020 deg.
Starting angle (2θ): 5 deg.
Stopping angle (2θ): 40 deg.
Divergence slit: 0.5 deg.
Scattering slit: 0.5 deg.
Receiving slit: 0.3 deg.
Curved monochromator: used.

The hydroxygallium phthalocyanine according to the present invention has an excellent function and performance as a photoconductor and is applicable for constituting a solar battery, a photosensor, a switching element, etc., in addition to an electrophotographic photosensitive member as described above.

The hydroxygallium phthalocyanine according to the present invention may be produced, e.g., through a process as described below.

A halogenated gallium phthalocyanine is subjected to an acid paste treatment (i.e., a method including dissolving the phthalocyanine in acid (e.g., sulfuric acid) and pouring the resultant solution into water to reprecipitate the crystal into a paste) to obtain pasty hydrous hydroxygallium phthalocyanine, which is then freeze-dried to obtain low-crystallinity hydroxygallium phthalocyanine. The resultant low-crystallinity hydroxygallium phthalocyanine is then subjected to milling in a dispersing medium which may preferably be an amide solvent, examples of which may include: acetamide, N,N-dimethylformamide, N,N-dimethylacetamide, N-methylformamide, N-methylacetamide, N-methylpropionamide, and formamide. The halogenated gallium phthalocyanine may be produced through various processes as described in JP-A 6-93203.

The milling referred to herein is a treatment performed by using a milling device, such as a sand mill or a ball mill, together with dispersion media, such as glass beads, steel beads, and alumina balls. The milling time may preferably be on the order of 4–24 hours while it can vary depending on the milling device used and the uniform determination thereof is difficult. Too long a milling time is not appropriate for production of the hydroxygallium phthalocyanine according to the present invention. The best result may be attained by controlling the milling time while checking the Bragg angle of a milled product sampled every 1 to 3 hours. The dispersing medium for the milling may preferably be used in an amount which is 5 to 30 times the low-crystallinity hydroxygallium phthalocyanine by weight.

A characteristic feature of the production process according to the present invention is the freeze drying of hydrous hydroxygallium phthalocyanine. A hydroxygallium phthalocyanine obtained without the freeze drying step fails to provide the strongest peak appearing at the Bragg angle (2θ±0.2 deg.) of 28.1 deg. By the freeze drying step, the water (or moisture) contained in the hydrous hydroxygallium phthalocyanine is sublimed. Accordingly, the condition for the freeze-drying is one for causing the sublimation of water. For example, a reduced pressure of at most 4 Torr after freezing of the hydrous hydroxygallium phthalocyanine may be appropriate and the sublimation may be thereafter continued even at room temperature.

In a specific example of the production process according to the present invention, a freeze drying apparatus ("KFD-1", available from Kaneda Rika K.K.) was used for the freeze drying while connecting a vacuum pump thereto. In the apparatus, the temperature at the water trap unit could be adjusted in the range of −20° to −110° C. The vacuum pump used exhibited a gas discharge rate of 100 liter/min. and an ultimate vacuum of $10^{-4}$ Torr.

The halogenated gallium phthalocyanine as a starting material can also be bromogallium phthalocyanine or iodogallium phthalocyanine in addition to chlorogallium phthalocyanine.

Next, some examples of application of the hydroxygallium phthalocyanine crystal as a charge-generating material in the electrophotographic photosensitive member will be described.

The electrophotographic photosensitive member according to the present invention may have a laminar structure including a single photosensitive layer containing both a charge-generating material and a charge-transporting material formed on an electroconductive support, or alternatively a laminar photosensitive layer including a charge generation layer containing a charge-generating material and a charge transport layer containing a charge-transporting material formed successively on an electroconductive support. The order of lamination of the charge generation layer and the charge transport layer can be reversed.

The electroconductive support may comprise any material exhibiting electroconductivity, examples of which may include: metals, such as aluminum and stainless steel; and solid substrates of, e.g., metals, plastics and paper, provided with an electroconductive coating layer. The electroconductive support may assume the form of a cylinder or a flat, curved or wound sheet or belt.

Between the electroconductive support and the photosensitive layer, it is possible to dispose a primer layer or undercoating layer having a barrier function and an adhesive function. The undercoating layer may for example comprise a material, such as polyvinyl alcohol, polyethylene oxide, ethyl cellulose, methyl cellulose, casein, polyamide, glue or gelatin. These materials may be dissolved in an appropriate solvent to be applied onto the electroconductive support, thereby forming a film in a thickness of, e.g., 0.2–3.0 $\mu$m.

The photosensitive layer when employed as a single layer may be formed by mixing the hydroxygallium phthalocyanine according to the present invention as a charge-generating material and a charge-transporting material into an appropriate binder resin solution to form a mixture liquid and applying the mixture liquid onto the electroconductive support, optionally via an undercoating layer as described above.

In the case of forming a laminar photosensitive layer as described above, the charge generation layer may suitably be formed by dispersing the hydroxygallium phthalocyanine according to the present invention in an appropriate binder solution to form a dispersion liquid and applying the dispersion liquid, followed by drying. However, the charge generating layer can also be formed by vapor deposition of the hydroxygallium phthalocyanine.

The charge transport layer may be formed by applying and drying a paint formed by dissolving a charge-transporting material and a binder resin in a solvent. Examples of the charge-transporting material may include: triarylamine compounds, hydrazone compounds, stilbene compounds, pyrazoline compounds, oxazole compounds, thiazole compounds, and triarylmethane compounds.

Examples of the binder for constituting the above-mentioned photosensitive layer or constituent layers thereof may include: polyesters, acrylic resin, polyvinylcarbazole, phenoxy resins, polycarbonates, polyvinyl butyral, polystyrene, polyvinyl acetate, polysulfone, polyarylate, vinylidene chloride-acrylonitrile copolymer, and polyvinyl benzal.

The application of the photosensitive layer(s) may be performed by coating methods, such as dipping, spray coating, spinner coating, bead coating, blade coating and beam coating.

The single-layered photosensitive layer may have a thickness of 5–40 $\mu$m, preferably 10–30 $\mu$m. In the laminar photosensitive layer, the charge generation layer may have a thickness of 0.1–10 $\mu$m, preferably 0.05–5 $\mu$m, and the charge transport layer may have a thickness of 5–40 $\mu$m, preferably 10–30 $\mu$m.

The charge-generating material may preferably be contained in 20–80 wt. %, more preferably 30–70 wt. %, of the charge generation layer. The charge-transporting material may preferably be contained in 20–80 wt. %, more preferably 30–70 wt. %, of the charge transport layer.

The single-layered photosensitive layer may preferably contain 3–30 wt. % of the charge-generating material and 30–70 wt. % of the charge-transporting material, respectively with respect to the total weight thereof.

The hydroxygallium phthalocyanine according to the present invention can be used in mixture with another charge-generating material if such is desired, e.g., for use in a panchromatic system or a digital analog combined system, or for improving the sensitivity or durability. In such cases, the hydroxygallium phthalocyanine may preferably constitute 50 wt. % of the total charge-generating materials.

The photosensitive layer may be further be coated with a protective layer as desired. Such a protective layer may be formed by applying a solution in an appropriate solvent of a resin, such as polyvinyl butyral, polyester, polycarbonate resin (such as polycarbonate Z and modified polycarbonate), nylon, polyimide, polyarylate, polyurethane, styrene-butadiene copolymer, styrene-acrylic acid copolymer or styrene-acrylonitrile copolymer onto a photosensitive layer, followed by drying. The protective layer may preferably be formed in a thickness of 0.05–20 $\mu$m. The protective layer can contain electroconductive particles or an ultraviolet absorber. The electroconductive particles may for example comprise particles of a metal oxide, such as tin oxide.

Next, some embodiments of structure and operation of the electrophotographic apparatus including an electrophotographic photosensitive member according to the present invention will be described.

Referring to FIG. 1, a drum-shaped photosensitive member 1 according to the present invention is driven in rotation at a prescribed peripheral speed in an indicated arrow direction about an axis 1$a$. During the rotation, the outer peripheral surface of the photosensitive member 1 is uniformly charged by charging means 2 at a prescribed positive or negative potential, and then exposed to light-image L (as by slit exposure or laser beam scanning exposure) by using an imagewise exposure means (not shown), whereby an electrostatic latent image corresponding to an exposure image is successively formed on the peripheral surface of the photosensitive member 1. The electrostatic latent image is then developed with a toner by developing means 4 to form a toner image on the photosensitive member 1. The toner image is transferred by corona transfer means 5 onto a recording material 9 which has been supplied from a paper supply unit (not shown) to a position between the photosensitive member 1 and the transfer means 9 in synchronism with the rotation of the photosensitive member 1. The recording material 9 carrying the received toner image is then separated from the photosensitive member surface and guided to an image fixing device 8 to fix the toner image. The resultant print or copy comprising the fixed toner image is then discharged out of the electrophotographic apparatus.

The surface of the photosensitive member 1 after the image transfer is subjected to removal of the residual toner by a cleaning means 6 to be cleaned and then subjected to charge removal by a pre-exposure means 7, to be recycled for repetitive image formation.

Figure 2:
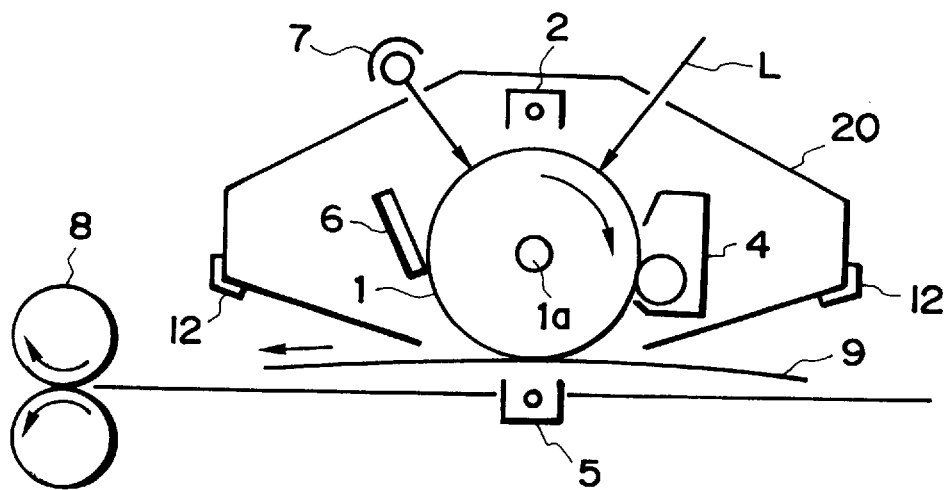

FIG. 2 shows another embodiment of the electrophotographic apparatus wherein at least a photosensitive member 1, a charging means 2 and a developing means 4 are housed within a container 20 to form a process cartridge, which is detachably mountable or insertable to a main assembly of the electrophotographic apparatus along a guide means 12, such as a guide rail, provided to the main assembly. A cleaning means 6 disposed within the container 20 in this embodiment can be omitted or disposed outside the container 20.

Figure 3:
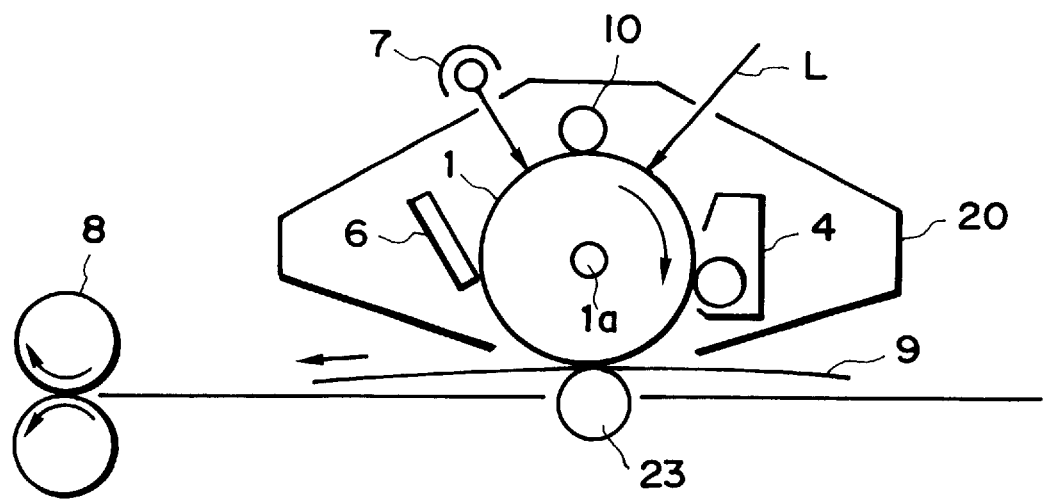
Figure 4:
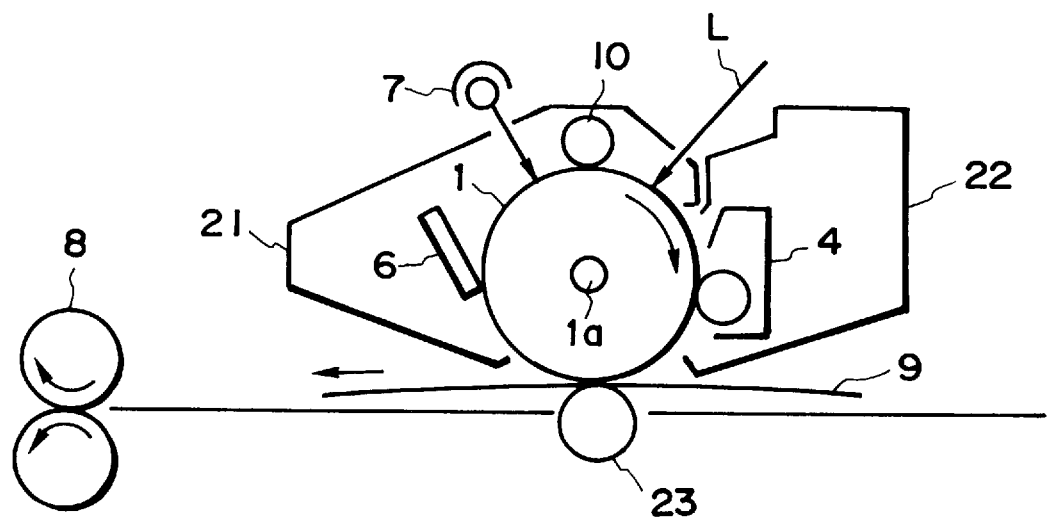

On the other hand, as shown in FIGS. 3 and 4, it is possible to use a direct charging member 10 and cause the direct charging member 10 supplied with a voltage to contact the photosensitive member 1 to charge the photosensitive member. (This mode may be referred to as a "direct charging" scheme.) In the apparatus shown in FIGS. 3 and 4, a toner image on the photosensitive member 1 is also transferred onto a recording material 9 by the action of a direct charging member 23. More specifically, by causing the direct charging member is supplied with a voltage while in contact with the recording material 9 to transfer the toner image on the photosensitive member 1 onto the recording material 9.

Further, in the apparatus shown in FIG. 4, at least the photosensitive member 1 and the direct charging member 10 are housed within a first container 21 to form a first process cartridge, and at least a developing means 4 is housed within a second vessel 22 to form a second process cartridge, so that the first and second process cartridges are detachably mountable to a main assembly of the apparatus. A cleaning means 6 can be disposed or not disposed within the container 21.

In case where the electrophotographic apparatus is used as a copying machine or a printer, exposure light image L may be provided as reflected light from or transmitted light through an original, or by converting data read from the original into a signal and effecting a laser beam scanning, a drive of an LED array or a drive of a liquid crystal shutter array.

Hereinbelow, the present invention will be described more specifically based on Examples and Comparative Examples. In the following description, "%" and "parts" used for describing compositions are all by weight.

EXAMPLE 1

Figure 5:
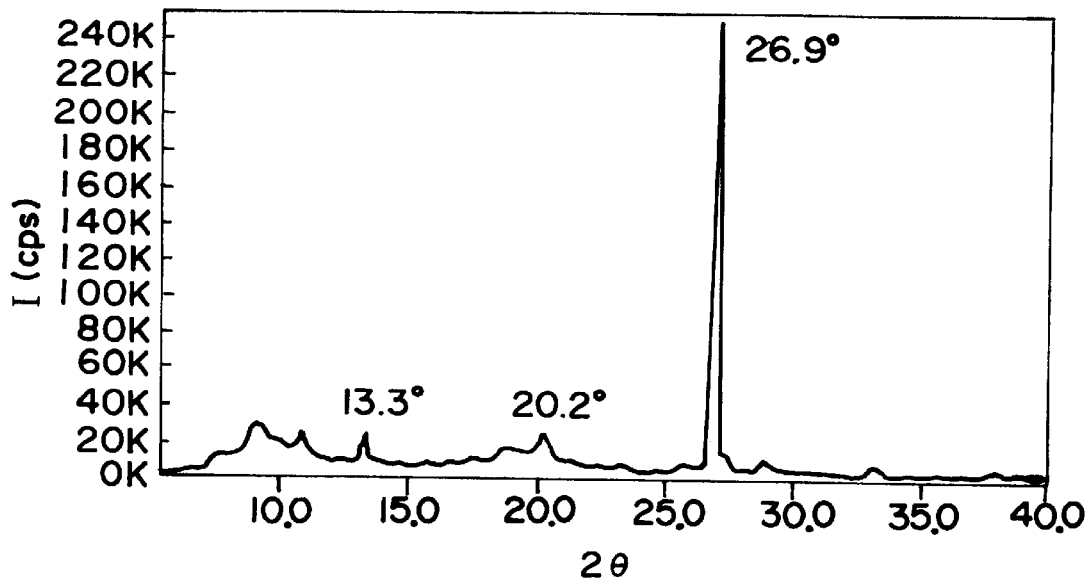
FIG. 5 is a graph showing a powder X-ray diffraction pattern of chlorogallium phthalocyanine crystal produced in Example 1.

73 g of o-phthalonitrile, 25 g of gallium trichloride and 400 ml of α-chloronaphthalene were reacted at 200° C. for 4 hours in a nitrogen atmosphere, and the product was recovered by filtration at 130° C. The product was washed by dispersing it in N,N-dimethylformamide at 130° C. for 1 hour, filtered, washed with methanol and dried to obtain 45 g of chlorogallium phthalocyanine crystal. The crystal exhibited a powdery X-ray diffraction pattern as shown in FIG. 5 and the following results by an elementary analysis:

|  | C (%) | H (%) | N (%) | Cl (%) |
| --- | --- | --- | --- | --- |
| Calculated value | 62.22 | 2.61 | 18.14 | 5.74 |
| Measured value | 61.78 | 2.66 | 18.28 | 6.25 |

Figure 6:
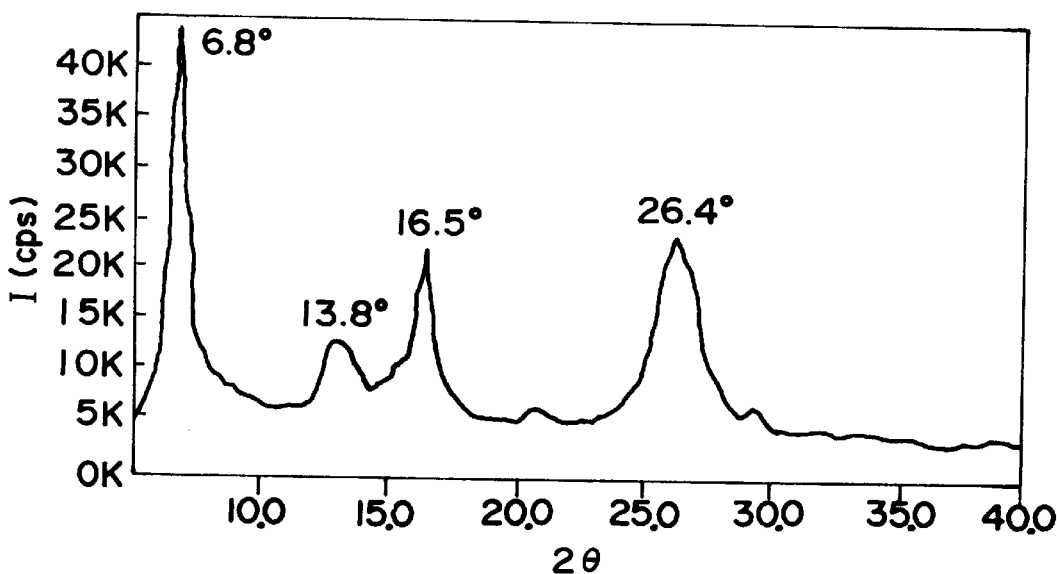
FIG. 6 is a graph showing a powder X-ray diffraction pattern of low-crystallinity hydroxygallium phthalocyanine crystal produced in Example 1.

15 g of the above-obtained chlorogallium phthalocyanine was dissolved in 450 g of conc. sulfuric acid at 10° C., and the resultant solution was added dropwise into 2300 g of ice water to reprecipitate the crystal, which was recovered by filtration. The crystal was washed by dispersion in 2%-ammonia water and then sufficiently washed with deionized water. The washed crystal was then frozen at liquid nitrogen temperature for ca. 3 min. and subjected to freeze drying by means of the above-mentioned freeze drying apparatus ("KFD-1", available from Kaneda Rika K.K.) at a vacuum of 1 mmHg to obtain 13 g of low-crystallinity hydroxygallium phthalocyanine, which exhibited a powder X-ray diffraction pattern as shown in FIG. 6.

Figure 7:
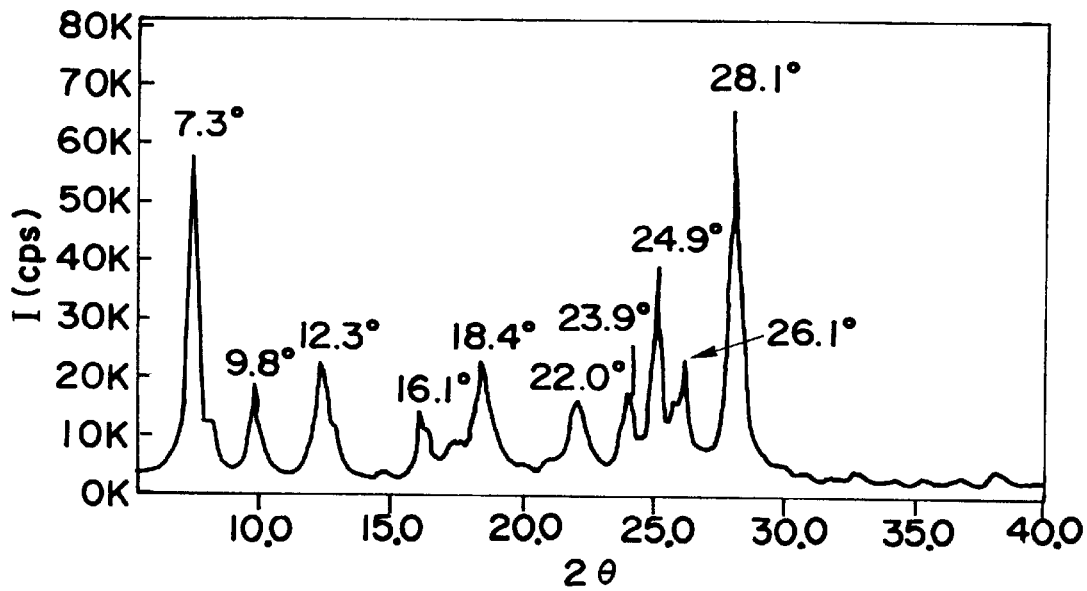
FIG. 7 is a graph showing a powder X-ray diffraction pattern of hydroxygallium phthalocyanine crystal having a crystal form according to the invention produced in Example 1.

Then, 7 g of the above-obtained hydroxygallium phthalocyanine and 210 g of N,N-dimethylformamide were subjected to milling together with 300 g of 1 mm-dia. glass beads in a sand mill at room temperature (22° C.) for 5 hours. From the dispersion liquid, a solid material was recovered, sufficiently washed with methanol and dried to obtain 5.6 g of a novel crystal form of hydroxygallium phthalocyanine according to the present invention, which exhibited a powder X-ray diffraction pattern as shown in FIG. 7. The X-ray diffraction pattern in FIG. 7 exhibits strong peaks at Bragg angles (2θ±0.2 deg.) of 7.3, 9.8, 12.3, 16.1, 18.4, 22.0, 23.9, 24.9, 26.1 and 28.1 deg. in which the strongest peak is at 28.1 deg. The hydroxygallium phthalocyanine also provided the following elementary analyst analysis results:

|  | C (%) | H (%) | N (%) | Cl (%) |
| --- | --- | --- | --- | --- |
| Calculated value | 64.14 | 2.86 | 18.70 | — |
| Measured value | 62.75 | 2.56 | 18.31 | 0.54 |

EXAMPLE 2

Figure 8:
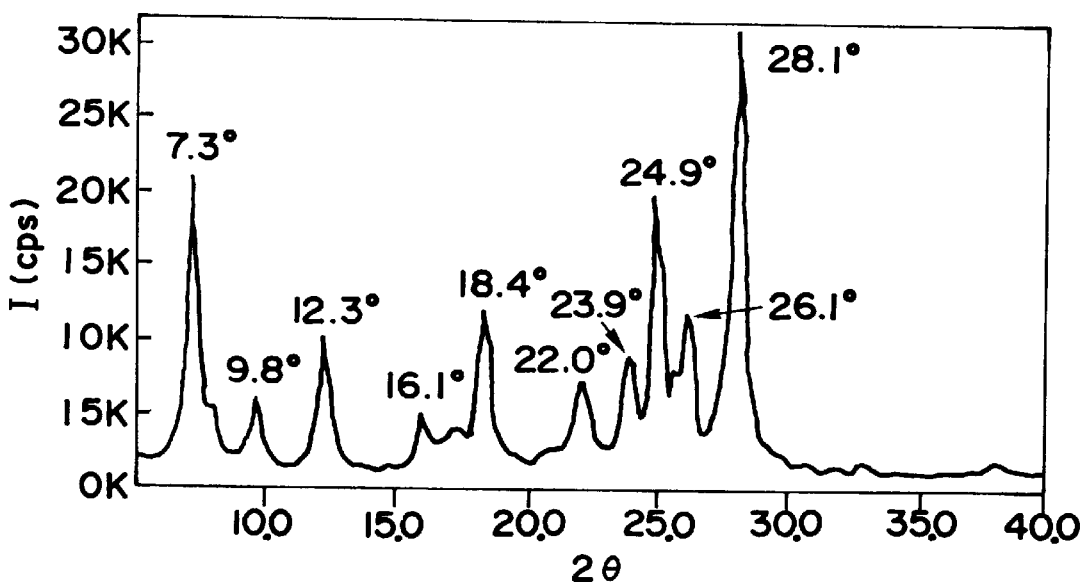
FIG. 8 is a graph showing a powder X-ray diffraction pattern of hydroxygallium phthalocyanine crystal having a crystal form according to the invention produced in Example 2.
Figure 9:
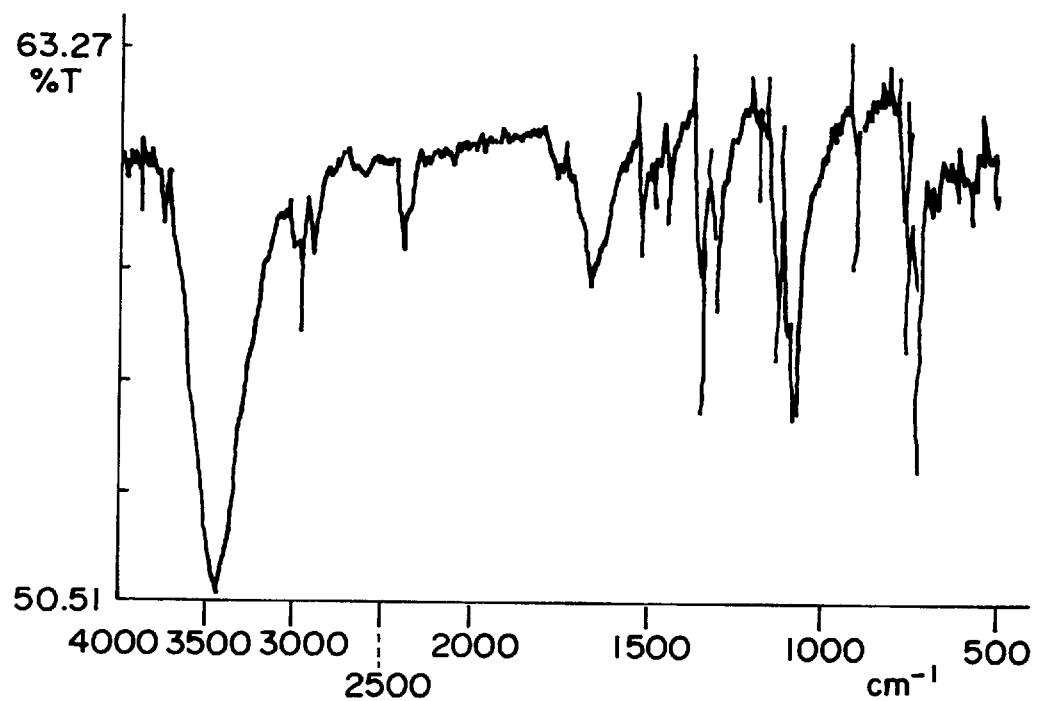
FIG. 9 is a graph showing an infrared absorption spectrum of hydroxygallium phthalocyanine crystal having a crystal form according to the invention produced in Example 2.

A hydroxygallium phthalocyanine exhibiting a powdery X-ray diffraction pattern as shown in FIG. 8 was prepared through the same process as in Example 1 except that the milling time was changed from 5 hours to 15 hours. The X-ray diffraction pattern in FIG. 8 exhibits strong peaks at Bragg angles (2θ±0.2 deg.) of 7.3, 9.8, 12.3, 16.1, 18.4, 22.0, 23.9, 24.9, 26.1 and 28.1 deg. in which the strongest peak is at 28.1 deg. The hydroxygallium phthalocyanine also provide an infrared absorption spectrum as shown in FIG. 9 and the following elementary analysis results:

|  | C (%) | H (%) | N (%) | Cl (%) |
| --- | --- | --- | --- | --- |
| Calculated value | 64.14 | 2.86 | 18.70 | — |
| Measured value | 62.19 | 2.70 | 18.06 | 0.54 |

COMPARATIVE EXAMPLE 1

30 g of 1,3-diiminoisoindoline, 9.1 g of gallium trichloride and 230 g of quinoline were reacted for 3 hours at 200° C. in a nitrogen atmosphere, and the product was recovered by filtration. The product was washed with acetone and methanol and dried to obtain 27 g of chlorogallium phthalocyanine, which exhibited a powder X-ray diffraction pattern similar to the one shown in FIG. 5.

Figure 10:
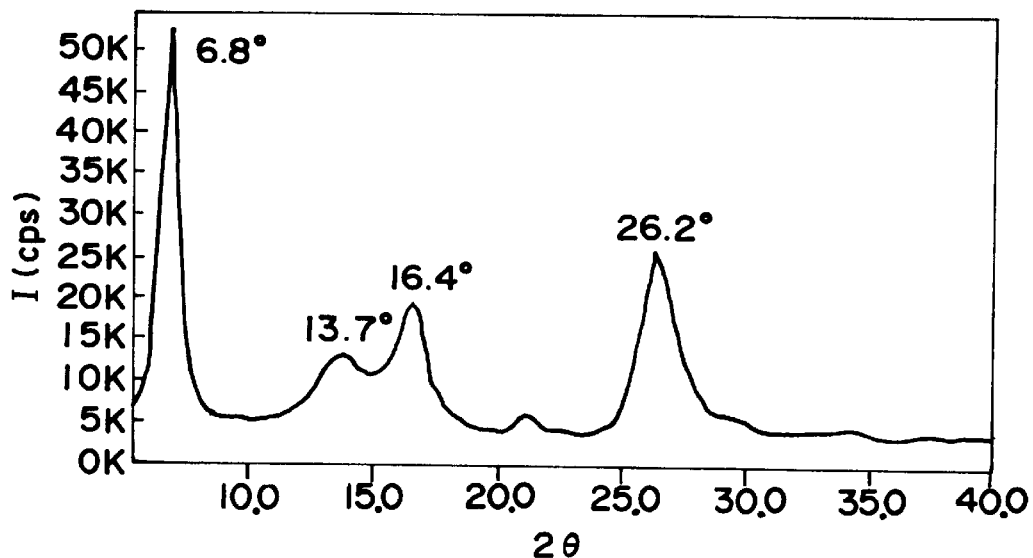
FIG. 10 is a graph showing a powder X-ray diffraction pattern of low-crystallinity hydroxygallium phthalocyanine crystal produced in Comparative Example 1.

15 g of the thus-obtained chlorogallium phthalocyanine was dissolved in 300 g of conc. sulfuric acid at 0° C., and the solution was added dropwise into 2250 g of distilled water at 5° C. under stirring to re-precipitate the crystal, which was recovered by filtration. The crystal was washed with distilled water and 2%-ammonia water and then dried under vacuum at ca. 40° C. for promoting the drying to obtain 13 g of low-crystallinity hydroxygallium phthalocyanine, which exhibited a powdery X-ray diffraction pattern shown in FIG. 10.

Figure 11:
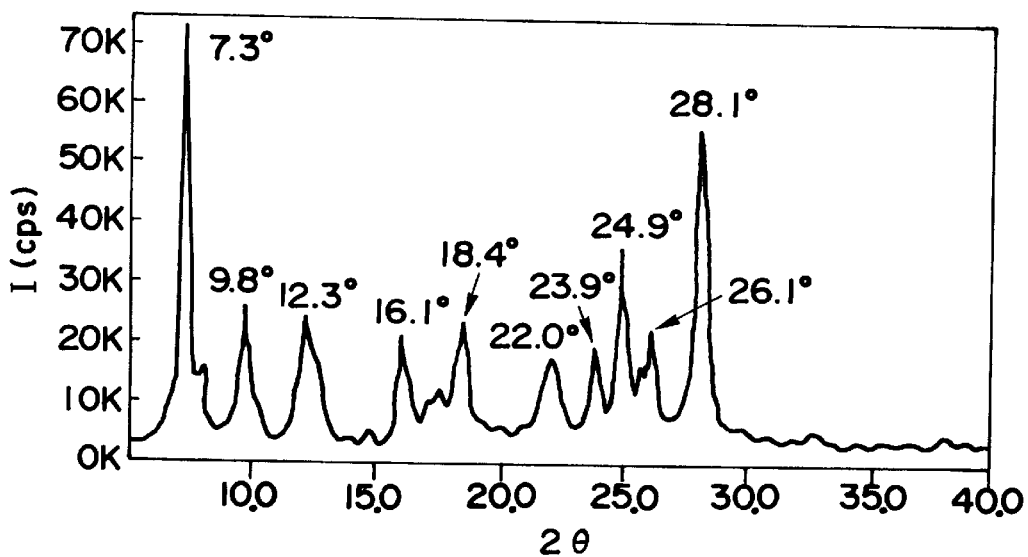
FIG. 11 is a graph showing a powder X-ray diffraction pattern of hydroxygallium phthalocyanine crystal produced in Comparative Example 1.

Then, 0.5 g of the resultant hydroxygallium phthalocyanine and 15 g of N,N-dimethylformamide were subjected to milling with 30 g of 1 mm-dia. glass beads for 10 hours within a paint shaker (available from K.K. Toyo Seiki Seisakusho) at a vibration speed of 750 cpm. From the resultant dispersion liquid, a solid matter was recovered, sufficiently washed with methanol and dried to obtain a crystal, which exhibited a powder X-ray diffraction pattern as shown in FIG. 11.

Hereinbelow, some examples for preparation of electrophotographic photosensitive members by using hydroxygallium phthalocyanines prepared above will be described.

EXAMPLE 3

50 parts of titanium oxide powder coated with tin oxide containing 10% of antimony oxide, 25 parts of resol-type phenolic resin, 20 parts of methyl cellosolve, 5 parts of methanol and 0.002 part of silicone oil (polydimethylsiloxane-polyoxyalkylene copolymer, Mw (weight-average molecular weight)=3,000) were dispersed for 2 hours together with 1 mm-dia. glass beads in a sand mill to prepare an electroconductive paint, which was applied by dipping onto an aluminum cylinder (30 mm-dia.× 260 mm) and dried at 140° C. for 30 min. to obtain a 20 um-thick electroconductive layer.

The aluminum cylinder with the electroconductive layer was further coated by dipping within a solution of 5 parts of 6-66-610-12 quaternary polyamide copolymer in a mixture solvent of 70 parts of methanol and 25 parts of butanol, followed by drying, to form a 1 μm-thick undercoating layer.

Separately, 3 parts of the hydroxygallium phthalocyanine prepared in Example 2 and 2 parts of polyvinyl butyral were added to 100 parts of cyclohexanone, and the mixture was subjected to dispersion together with 1 mm-dia. glass beads for 1 hour within a sand mill. The resultant dispersion was diluted with 100 parts of methyl ethyl ketone to form a coating liquid. The coating liquid was applied by dipping onto the undercoating layer and dried at 90° C. for 10 min. to form a 0.15 μm-thick charge generation layer.

Separately, 10 parts of a charge-transporting material of the following structural formula:

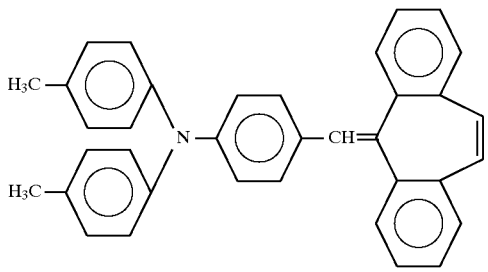

and 10 parts of bisphenol Z-type polycarbonate resin were dissolved in 60 parts of chlorobenzene to form a coating liquid, which was then applied by dipping onto the charge generation layer and dried at 110° C. for 1 hour to form a 20 μm-thick charge transport layer, thereby preparing an electrophotographic photosensitive member.

EXAMPLE 4

An electrophotographic photosensitive member was prepared in the same manner as in Example 3 except for using the hydroxygallium phthalocyanine produced in Example 1 instead of the hydroxygallium phthalocyanine of Example 2 as a charge-generating material.

COMPARATIVE EXAMPLE 2

An electrophotographic photosensitive member was prepared in the same manner as in Example 3 except for using the hydroxygallium phthalocyanine produced in Comparative Example 1 instead of the hydroxygallium phthalocyanine of Example 2 as a charge-generating material.

The photosensitive members prepared in Examples 3 and 4 and Comparative Example 2 were respectively set in a laser beam printer "LBP-SX", available from Canon K.K.) and subjected to a sensitivity measurement wherein each photosensitive member was charged to a set dark potential of −700 volts and then illuminated with laser light having a wavelength of 820 nm to measure an exposure light quantity required for lowering the potential from −700 volts to −150 volts as a photosensitivity. The results are shown in Table 1 below:

TABLE 1

| Photosensitive member | Exposure quantity ($\mu J/cm^2$) |
|---|---|
| Example 3 | 0.28 |
| Example 4 | 0.29 |
| Comparative Example 2 | 0.33 |

The three laser beam printers including the photosensitive members of Examples 3 and 4 and Comparative Example 2 respectively were subjected to a continuous image formation test on 4000 sheets while initially setting a dark-part potential ($V_D$) and a light part potential ($V_L$) to −700 volts and −150 volts, respectively, to measure the dark-part potential ($V_D$) and the light-part potential ($V_L$) after the continuous image formation test. The results are shown in Table 2 below.

TABLE 2

| Photosensitive | Initial | | After 4000 sheets | |
|---|---|---|---|---|
| member | $V_D$ (V) | $V_L$ (V) | $V_D$ (V) | $V_L$ (V) |
| Example 3 | −700 | −150 | −705 | −160 |
| Example 4 | −700 | −150 | −705 | −160 |
| Comparative Example 3 | −700 | −150 | −680 | −230 |

Three additional photosensitive members were prepared in the same manner as in Examples 3 and 4 and Comparative Example 2, respectively, and a part of each of the photosensitive members was irradiated with white light of 3000 lux for 30 min. The photosensitive members were respectively incorporated in a laser beam printer otherwise identical to the above and the dark part potentials of each photosensitive member were measured with respect to the irradiated part and the non-irradiated part while setting the dark-part potential at the non-irradiated part at −700 volts. The results are shown in Table 3 below:

TABLE 3

| Photosensitive member | Non-irradiated part (V) | Irradiated part (V) | Difference (V) |
|---|---|---|---|
| Example 3 | −700 | −675 | 25 |
| Example 4 | −700 | −670 | 30 |
| Comparative Example 3 | −700 | −630 | 70 |

EXAMPLE 6

An electrophotographic photosensitive member was prepared in the same manner as in Example 3 except for replacing the polyvinyl butyral resin (binder resin) used in Example 3 with bisphenol Z-type polycarbonate resin.

EXAMPLE 7

An electrophotographic photosensitive member was prepared in the same manner as in Example 3 except for replacing the charge-transporting material with a compound of the following formula:

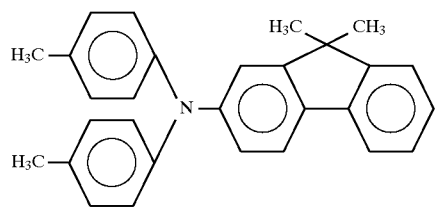

EXAMPLE 8

An electrophotographic photosensitive member was prepared in the same manner as in Example 3 except for replacing the charge-transporting material with a compound of the following formula:

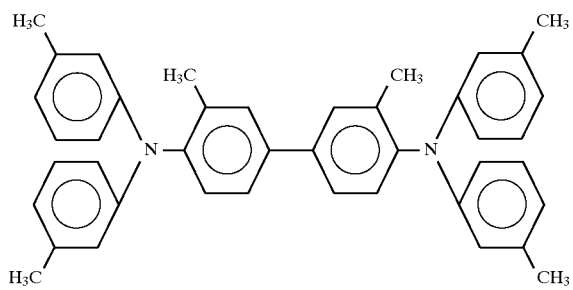

The above-prepared three photosensitive members of Examples 5–7 were respectively incorporated in laser beam printers as described above to measure the photosensitivity in terms of an exposure light quantity required for lowering the dark-part potential of −700 volts to −150 volts. The results are shown in Table 4 below:

TABLE 5

| Photosensitive member | Exposure quantity ($\mu J/cm^2$) |
| --- | --- |
| Example 5 | 0.27 |
| Example 6 | 0.27 |
| Example 7 | 0.26 |

What is claimed is:

1. An electrophotographic photosensitive member comprising: an electroconductive support and at least a photosensitive layer formed on the electroconductive support, said photosensitive layer containing a hydroxygallium phthalocyanine having a crystal form characterized by strong peaks at Bragg angles (2θ±0.2 deg.) of 7.3, 9.8, 12.3, 16.1, 18.4, 22.0, 23.9, 24.9, 26.1 and 28.1 deg. in a $CuK_\alpha$ characteristic X-ray diffraction pattern in which the strongest peak is at 28.1 deg.

2. A photosensitive member according to claim 1, wherein said photosensitive layer has a laminate structure including a charge generation layer and a charge transport layer, and said hydroxygallium phthalocyanine is contained in the charge generation layer.

3. A photosensitive member according to claim 2, wherein said charge generation layer comprises a mixture of a binder selected from polyvinyl butyral or bisphenol Z polycarbonate and the hydroxygallium phthalocyanine dispersed in the binder.

4. A photosensitive member according to claim 2, wherein said charge transport layer contains a charge-transporting material of the following formulae (a), (b) or (c):

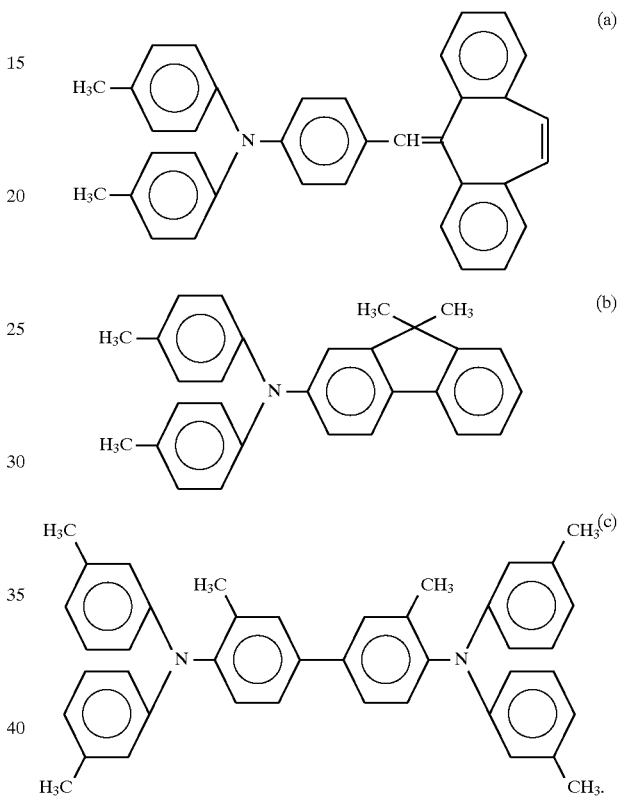

5. An electrophotographic apparatus, comprising:

an electrophotographic photosensitive member according to claim 1, charging means for charging the photosensitive member, imagewise exposure means for exposing imagewise the photosensitive member to form an electrostatic latent image into the photosensitive member, and developing means for developing the electrostatic latent image on the photosensitive member with a toner.

6. A process cartridge, comprising: an electrbphotographic photosensitive member according to claim 1 and a charging means for charging the photosensitive member so as to form an integral unit, which is detachably mountable to a main assembly of an electrophotographic apparatus.

7. A process cartridge according to claim 6, further including a developing means for developing an electrostatic latent image formed on the photosensitive member.

* * * * *

UNITED STATES PATENT AND TRADEMARK OFFICE
CERTIFICATE OF CORRECTION

PATENT NO. : 5,885,737
DATED : March 23, 1999
INVENTOR(S) : MASATO TANAKA

Page 1 of 2

It is certified that error appears in the above-identified patent and that said Letters Patent is hereby corrected as shown below:

ON THE COVER PAGE AT [56] REFERENCES CITED

Under U.S. Patent Document

"Amayama et al." should read --Anayama et al.--.

COLUMN 1

Line 44, "$\delta$-form," should read --$\epsilon$ form,--.

COLUMN 7

Line 24, "by causing" should be deleted.
Line 25, "member" should read --member 23--.

COLUMN 8

Line 24, "analyst" should be deleted.
Line 43, "provide" should read --provided--.
Line 63, "re-precipitate" should read --reprecipitate--.

UNITED STATES PATENT AND TRADEMARK OFFICE
CERTIFICATE OF CORRECTION

PATENT NO. : 5,885,737

DATED : March 23, 1999

INVENTOR(S) : MASATO TANAKA

It is certified that error appears in the above-identified patent and that said Letters Patent is hereby corrected as shown below:

<u>COLUMN 12</u>

Line 54, "electrbphoto-" should read --electrophoto--.

Signed and Sealed this

Seventh Day of December, 1999

Attest:

Attesting Officer

Q. TODD DICKINSON

Acting Commissioner of Patents and Trademarks